United States Patent
Bischoff et al.

(10) Patent No.: US 8,597,281 B2
(45) Date of Patent: Dec. 3, 2013

(54) METHOD AND DEVICE FOR PRODUCING CUTS IN A TRANSPARENT MATERIAL

(75) Inventors: Mark Bischoff, Jena (DE); Dirk Mühlhoff, Ot Riechheium (DE); Mario Gerlach, Altenberga (DE); Carsten Lang, Bad Köstritz (DE); Markus Sticker, Jena (DE); Michael Bergt, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1153 days.

(21) Appl. No.: 10/566,008

(22) PCT Filed: Jun. 29, 2004

(86) PCT No.: PCT/EP2004/007045
§ 371 (c)(1),
(2), (4) Date: Apr. 11, 2008

(87) PCT Pub. No.: WO2005/018516
PCT Pub. Date: Mar. 3, 2005

(65) Prior Publication Data
US 2008/0243109 A1    Oct. 2, 2008

(30) Foreign Application Priority Data
Jul. 25, 2003 (DE) .................................. 103 34 109

(51) Int. Cl.
*A61F 9/01* (2006.01)

(52) U.S. Cl.
USPC .................................. 606/5; 606/4; 128/898

(58) Field of Classification Search
USPC .......................................... 128/898; 606/4–6
See application file for complete search history.

(56) References Cited

U.S. PATENT DOCUMENTS

| | | | | |
|---|---|---|---|---|
| 5,364,388 A | * | 11/1994 | Koziol | 606/5 |
| 5,984,916 A | | 11/1999 | Lai | |
| 6,099,522 A | | 8/2000 | Knopp et al. | |
| 6,110,166 A | | 8/2000 | Juhasz | |
| 6,132,424 A | * | 10/2000 | Tang | 606/13 |
| 6,210,401 B1 | | 4/2001 | Lai | |
| 6,706,036 B2 | | 3/2004 | Lai | |
| 2003/0014042 A1 | | 1/2003 | Juhasz et al. | |
| 2003/0229339 A1 | * | 12/2003 | Bille | 606/5 |
| 2004/0039378 A1 | * | 2/2004 | Lin | 606/6 |
| 2005/0090813 A1 | | 4/2005 | Schweitzer et al. | |

FOREIGN PATENT DOCUMENTS

| | | |
|---|---|---|
| DE | 101 62 166 A1 | 6/2003 |
| EP | 1 279 386 A1 | 1/2003 |
| WO | WO 99/27996 | 6/1999 |
| WO | WO 03/082156 A2 | 10/2003 |

OTHER PUBLICATIONS

Heisterkamp et al., "Optimierung der Laserparameter für die intrastromale Schnittfuhrung mittels ultrakurzer Laserpulse", Ophthalmologe, 2001, 98:623-628.

* cited by examiner

*Primary Examiner* — Bil Thomson
*Assistant Examiner* — Jeffrey Lipitz
(74) *Attorney, Agent, or Firm* — Patterson Thuente Pedersen, P.A.

(57) ABSTRACT

The invention relates to a method for producing cuts in a transparent material, in particular in the cornea, by creating optical openings in said material by means of laser radiation that is focused in said material, whereby the focal point is displaced in order to produce the cut from a surface grid-type array of optical openings arranged in sequence. The focal point is displaced along a trajectory and optical openings along said trajectory that are adjacent are not produced immediately after one another. In addition, the surface grid-type array of optical openings is constructed from at least two sub-grids, the optical openings of which are processed sequentially grid by grid.

19 Claims, 2 Drawing Sheets

METHOD AND DEVICE FOR PRODUCING CUTS IN A TRANSPARENT MATERIAL

FIELD OF THE INVENTION

The invention relates to a method of producing cuts in a transparent material, in particular in the cornea of the eye, by generating optical breakthroughs in the material by means of laser radiation focused into the material, the focal point being shifted so as to form the cut by a surface lattice-type array of sequentially arranged optical breakthroughs, wherein the focal point is shifted along a path and adjacent optical breakthroughs are not generated immediately following each other along said path. The invention further relates to a device for producing cuts in a transparent material, in particular in the cornea of the eye, comprising a source of laser radiation which focuses laser radiation into the material and causes optical breakthroughs therein, wherein a scanning unit which shifts the focal point, and a control unit, which controls the scanning unit, are provided so as to form the cut by a surface lattice-type array of sequentially arranged optical breakthroughs in the material, said control unit shifting the focal point along a path and not generating adjacent optical breakthroughs immediately following each other along said path.

BACKGROUND OF THE INVENTION

Curved cuts within a transparent material are generated, in particular, in laser-surgical methods, especially in ophthalmic surgery. This involves focusing treatment laser radiation within the tissue, i.e. beneath the tissue surface, so as to form optical breakthroughs in the tissue.

In the tissue, several processes initiated by the laser radiation occur in a time sequence. If the power density of the radiation exceeds a threshold value, an optical breakthrough will result, generating a plasma bubble in the material. After the optical breakthrough has been generated, said plasma bubble grows due to expanding gases. If the optical breakthrough is not maintained, the gas generated in the plasma bubble will be absorbed by the surrounding material, and the bubble disappears again. However, this process takes very much longer than the forming of the bubble itself. If a plasma is generated at a material boundary, which may also be located within a material structure as well, material will be removed from said boundary. This is then referred to as photo ablation. In connection with a plasma bubble which separates material layers that were previously connected, one usually speaks of photo disruption. For the sake of simplicity, all such processes are summarized here by the term optical breakthrough, i.e. said term includes not only the actual optical breakthrough, but also the effects resulting therefrom in the material.

For a high accuracy of a laser surgery method, it is desirable to guarantee high localization of the effect of the laser beams and to avoid collateral damage to adjacent tissue as far as possible. It is therefore common in the prior art to apply the laser radiation in pulsed form, so that the threshold value for the power density of the laser radiation required to cause an optical breakthrough is exceeded only during the individual pulses. In this regard, U.S. Pat. No. 5,984,916 clearly shows that the spatial extent of the optical breakthrough (in this case, of the generated interaction) strongly depends on the pulse duration. Therefore, high focusing of the laser beam in combination with very short pulses allows to place the optical breakthrough in a material with great point accuracy.

The use of pulsed laser radiation has recently become established practice particularly for laser-surgical correction of visual defects in opthalmology. Visual defects of the eye often result from the fact that the refractive properties of the cornea and of the lens do not cause optimal focusing on the retina.

U.S. Pat. No. 5,984,916 mentioned above, as well as U.S. Pat. No. 6,110,166, describe methods of producing cuts by means of suitable generation of optical breakthroughs, so that, ultimately, the refractive properties of the cornea are selectively influenced. A multitude of optical breakthroughs are sequentially arranged such that a lens-shaped partial volume is isolated within the cornea of the eye. The lens-shaped partial volume which is separated from the remaining corneal tissue is then removed from the cornea through a laterally opening cut. The shape of the partial volume is selected such that, after removal, the shape and, thus, the refractive properties of the cornea are modified such that the desired correction of the visual defect is effected. The cuts required here are curved, which makes a three-dimensional shifting of the focus necessary. Therefore, a two-dimensional deflection of the laser radiation is combined with simultaneous shifting of the focus in a third spatial direction.

When producing a cut by a series of optical breakthroughs in the material, an optical breakthrough is generated several times faster than it takes until a plasma generated therefrom is absorbed by the tissue again. It is known from the publication by A. Heisterkamp, et al., Der Opthalmologe, 2001, 98:623-628, that after an optical breakthrough has been generated in the cornea of the eye a plasma bubble grows at the focal point where the optical breakthrough was generated, which plasma bubble reaches a maximum size after a few us and then almost completely collapses again. This then leaves only small residual bubbles. Said publication states that joining of growing plasma bubbles reduces the quality of the cut. Therefore, it suggests a method of the above-mentioned type, wherein individual plasma bubbles are not generated directly next to each other. Instead, a gap is left between sequentially generated optical breakthroughs, which breakthroughs are generated along a spiral-shaped path. The gap is filled, in a second pass, through the spiral with optical breakthroughs and with plasma bubbles resulting therefrom. This is intended to prevent joining of adjacent plasma bubbles and to promote the quality of the cut. In the spiral described by Heisterkamp et al., the distance of the generated optical breakthroughs inevitably increases with the spiral windings.

As an alternative to the approach described in the cited publication, it could also be contemplated to make the time interval between subsequently generated optical breakthroughs so large that the plasma bubble of one optical breakthrough has already collapsed before the next optical breakthrough is generated. However, this would considerably slow down the production of the cut.

Generating cuts quickly is desirable not only for convenience or in order to save time; bearing in mind that movements of the eye inevitably occur during ophthalmic operations, quick generation of cuts also improves the optical quality of the result thus achieved and reduces the requirement to track eye movements.

Therefore, it is an object of the invention to improve a method and a device of the above-mentioned type such that generating good-quality cuts requires as little time as possible.

SUMMARY OF THE INVENTION

According to the invention, the object is achieved by a method of the above-mentioned type, wherein the surface lattice-type array of the optical breakthroughs is made up of at least two partial lattices, which are processed one after the other, with respect to their associated optical breakthroughs.

The object is further achieved by a device of the aforementioned type, wherein the surface lattice-type array of the optical breakthroughs is made up of at least two partial lattices, and the control unit effects focus shifting such that the partial lattices are processed one after each the other with respect to their associated optical breakthroughs.

By dividing the cut into a plurality of partial lattices, the invention has the effect, on the one hand, that there is no danger of generating directly adjacent breakthroughs, immediately after each other in time, while serially arranging the optical breakthroughs. On the other hand, complete and/or uniform filling of the cut surface with optical breakthroughs is achieved.

The surface cut to be generated by serial arrangement of optical breakthroughs is generally a curved surface. On the curved surface, a regular surface lattice is defined so as to achieve uniform and preferably tight packing of zones in which optical breakthroughs are effective. In doing so, care is taken, in particular, that the spherical distance between the centers of two optical breakthroughs (also referred to as geodesic line) exceeds the distance of the locations of optical breakthroughs in space only by a maximum of 10%. Under these prerequisites, a small area of the cut may be regarded as a planar surface portion in good approximation. Therefore, a "surface lattice-type array" is understood to be the regular arrangement of those locations where the optical breakthroughs are initiated by focusing of the laser radiation, relative to the cut in three-dimensional space. In connection with the above-mentioned approximation, a planar surface element may be assumed at least in portions of the surface.

Suitable division of the surface arrangement of the plasma bubbles into partial lattices and sequential processing of the partial lattices, i.e. first generating the breakthroughs of one partial lattice before initiating the breakthroughs of the next partial lattice, has the effect that there is always a spatial distance between two breakthroughs generated directly following each other in time. This avoids the problem that plasma bubbles of breakthroughs immediately following each other grow together. Additionally, individual partial lattices need not be completed.

As the speed at which optical breakthroughs are generated increases, plasma bubbles of optical breakthroughs which are adjacent due to the sequential arrangement of different portions of the path line may also grow together. The division of the surface lattice-type arrangement into at least two partial lattices avoids this problem, as it can be ensured by suitable selection of the partial lattices that no immediately adjacent optical breakthroughs are generated within one partial lattice. Further, a suitable selection of the partial lattices allows a uniform or even surface filling. In a preferred embodiment of the invention, it is envisaged that the partial lattices be selected such that, within the surface lattice-type arrangement for at least one optical breakthrough, in at least one partial lattice, all adjacent optical breakthroughs belong to one or more of the other partial lattices. This approach will conveniently be embodied such that, for all partial lattices, the optical breakthroughs do not have an immediately adjacent optical breakthrough which belongs to the same partial lattice. By this further embodiment, the speed at which the breakthroughs are generated one after the other is limited, with respect to the problem of plasma bubbles growing together, only by the time interval between two partial lattices. Using the values for the growth and collapse of a plasma bubble as published by Heisterkamp et al., the first plasma bubbles of sequential partial lattices should be at least about 2 to 5 μs or even a few milliseconds to seconds apart.

In principle, the number of partial lattices is not limited. However, it has turned out that, in the case of two partial lattices, it can sometimes not be completely avoided that plasma bubbles belonging to the same partial lattice are adjacent each other. Therefore, a division into three partial lattices is advantageous. A particularly advantageous surface lattice-type arrangement is the trigonal or hexagonal lattice (for better illustration, the common terms for the planar surface lattice are used herein), wherein not only very high surface filling of over 90% can be achieved, but wherein it is also ensured in a simple manner that an optical breakthrough belonging to a partial lattice only has immediate neighbors from the other two partial lattices.

The different partial lattices can be conveniently generated from a partial lattice template, which is displaced according to the number of partial lattices, in order to achieve the surface lattice-type arrangement. This approach further has the advantage that the control unit can effect focus shifting according to a fixed scheme associated with the partial lattice template, said scheme having the shape, e.g., of a particular scanning path or of a particular raster-scanning mode, respectively, and that it only has to consider a relatively simple coordinate transformation, e.g. in the form of a displacement, for the individual partial lattices.

BRIEF DESCRIPTION OF THE DRAWINGS

For the device according to the invention, any control unit is suitable which executes the process as explained, such as, for example, a suitably programmed micro-processor or computer which suitably controls the components of the device.

The invention will be explained in more detail below, by way of example and with reference to the Figures, wherein.

DETAILED DESCRIPTION OF THE INVENTION

Figure 1:
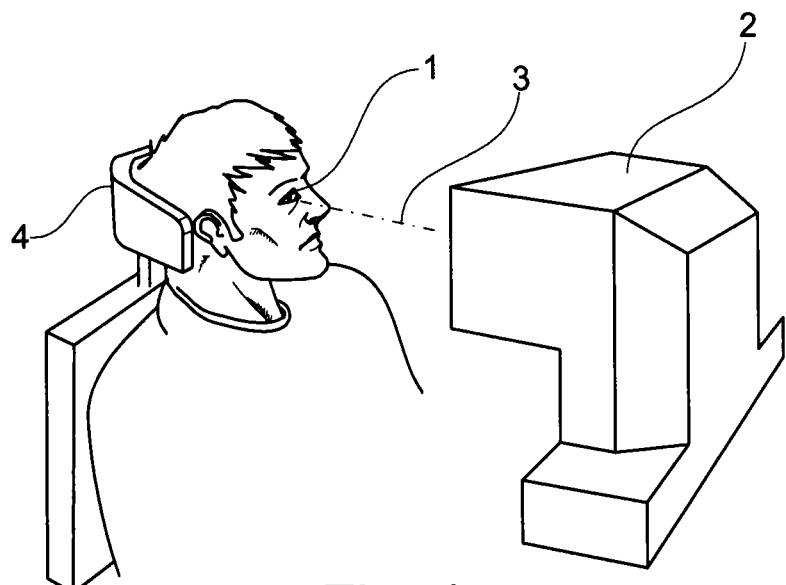
FIG. 1 is a perspective view of a patient during a laser-surgical treatment with a laser-surgical instrument.

FIG. 1 shows a laser-surgical instrument for treatment of an eye 1 of a patient, said laser-surgical instrument 2 serving to effect a refractive correction. For this purpose, the instrument 2 emits a treatment laser beam 3 onto the eye of the patient 1 whose head is immobilized in a head holder 4. The laser-surgical instrument 2 is capable of generating a pulsed laser beam 3 so that the method described in U.S. Pat. No. 6,110,166 can be carried out. The components of the instrument 2 are controlled by a control unit which is integrated according to the described embodiment.

Figure 2:
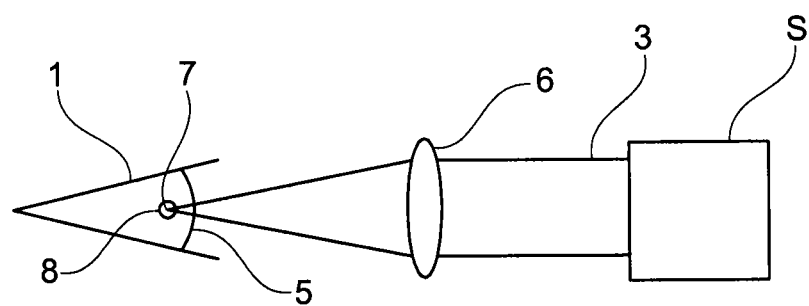
FIG. 2 depicts the focusing of a ray bundle onto the eye of the patient with the instrument of FIG. 1.

For this purpose, as schematically shown in FIG. 2, the laser-surgical instrument 2 comprises a source of radiation S whose radiation is focused into the cornea 5 of the eye 1. A visual defect in the eye 1 of the patient is remedied by means of the laser-surgical instrument 2 to remove material from the cornea 5 so that the refractive characteristics of the cornea are modified by a desired amount. In doing so, the material is removed from the corneal stroma, which is located beneath the epithelium and Bowman's membrane and above Descemet's membrane and the endothelium.

Material removal is effected in that layers of tissue are separated by focusing the high-energy pulsed laser beam 3 by means of an adjustable telescope 6 in a focus 7 located in the cornea 5. Each pulse of the pulsed laser radiation 3 generates an optical breakthrough in the tissue, said breakthrough initiating a plasma bubble 8. As a result, the tissue layer separation covers a larger area than the focus 7 of the laser radiation 3. By suitable deflection of the laser beam 3, many plasma bubbles 8 are now generated during treatment. These plasma bubbles 8 then form a cut 9, which circumscribes a partial volume T of the stroma, namely the material to be removed from the cornea 5.

Due to the laser radiation 3, the laser-surgical instrument 2 operates in the manner of a surgical knife which, without injuring the surface of the cornea 5, separates material layers within the cornea 5. If the cut is guided up to the surface of the cornea 5 by generating further plasma bubbles 8, material of the cornea 5 isolated by the cut 9 can be extracted laterally and, thus, removed.

Figure 3:
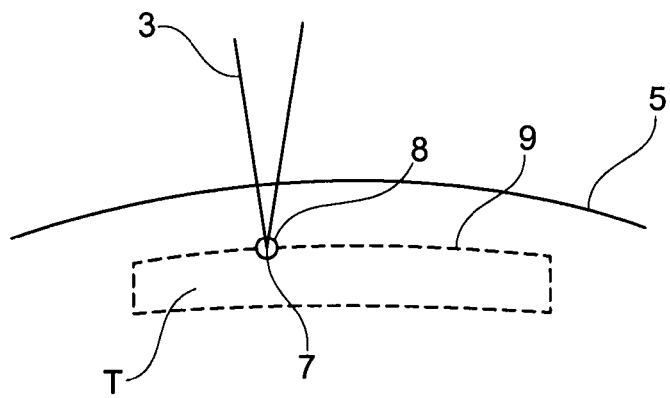
FIG. 3 is a schematic representation explaining a cut generated during laser-surgical treatment with the instrument of FIG. 1.

The generation of the cut 9 by means of the laser-surgical instrument 2 is schematically shown in FIG. 3. The cut 9 is formed by sequential arrangement of plasma bubbles 8 produced as a result of continuous displacement of the focus 7 of the pulsed focused laser beam 3.

Figure 4:
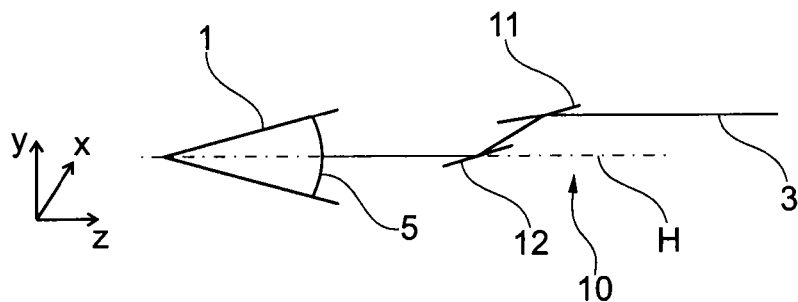
FIG. 4 depicts a deflection device of the laser-surgical instrument of FIG. 1.

On the one hand, the focus displacement according to one embodiment is effected by means of the deflecting unit 10, schematically shown in FIG. 4, which deflects the laser beam 3 along two mutually perpendicular axes, said laser beam 3 being incident on the eye 1 on a main axis of incidence H. For this purpose, the deflecting unit 10 uses a line mirror 11 as well as an image mirror 12, thus resulting in two spatial axes of deflection which are located behind each other. The point where the principal beam axis H and the deflection axis cross is then the respective point of deflection. On the other hand, the telescope 6 is suitably shifted for focus displacement. This allows shifting of the focus 7 along three orthogonal axes in the x/y/z coordinate system schematically shown in FIG. 4. The deflecting unit 10 shifts the focus in the x/y plane, with the line mirror allowing shifting of the focus in the x-direction and the image mirror allowing shifting of the focus in the y-direction. In contrast thereto, the telescope 6 acts on the z-coordinate of the focus 7.

Due to the corneal curvature, which is between 7 and 10 mm, the partial volume T is also curved accordingly. Thus, the corneal curvature leads to an image field curvature. This is taken into account by suitable control of the deflecting unit 10 and of the telescope 6.

If a cut as shown in FIG. 3 is curved in the same direction as the corneal surface, this may be achieved by an optical system whose image field curvature is similar to the curvature of the cornea, without the guide of the focus 7 having to take this into account.

Figures 5A, 5B:
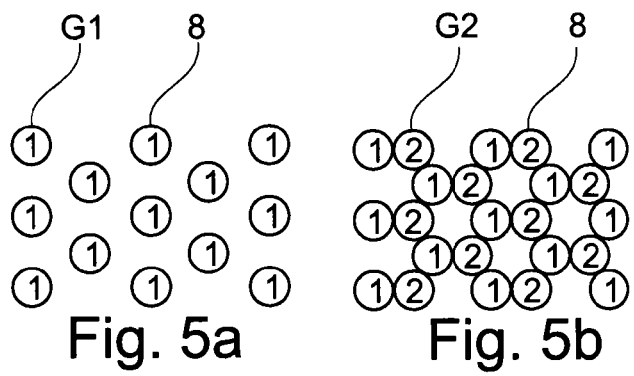
FIG. 5 depicts three partial FIGS. 5a, 5b and 5c concerning the assembly of the cut of FIG. 3 from a plurality of partial lattices.
Figure 5C:
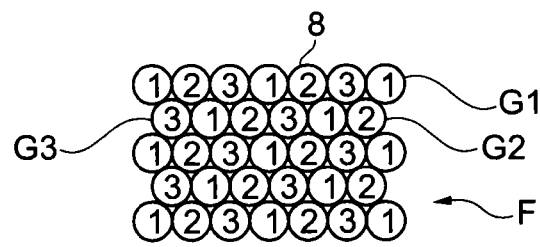

The curved cut 9 is generated by sequential arrangement of plasma bubbles 8 by suitable shifting of the focus 7 as well as control of the source of radiation S. In doing so, for example, raster-scanning of the cut 9 may be effected. However, the control unit of the instrument 2 controls the deflecting unit 10 and the scanning optics 6 such that no immediately adjacent breakthroughs form within a certain time frame. The arrangement of the plasma bubbles 8 which form the cut 9 may be regarded as a (curved) surface lattice-type arrangement F. For illustration, a planar representation was chosen for the surface lattice-type array F in FIG. 5; in reality, the individual plasma bubbles 8 are, of course, arranged on a spatially curved surface in order to isolate the partial volume T. Now, the surface lattice-type array F thus defined on the curved cut 9 is not generated by immediately sequential processing of the plasma bubbles 8 located therein, but instead, the control unit of the instrument 2 divides the surface lattice-type array F into three partial lattices G1, G2 and G3, which are shown in FIGS. 5a to 5c. The partial lattices G1 and G2 as well as G3 are obtained from a common lattice template, which is respectively displaced along a lattice axis by the distance between two plasma bubbles 8.

The control unit now raster-scans the individual points of the surface lattice-type arrangement F such that the points of the partial lattice G1 are processed first. Once a plasma bubble 8 has been generated at each point of the partial lattice G1, the control unit effects coordinate displacement with respect to the grid pattern of the partial lattice G1 and generates optical breakthroughs according to the partial lattice G2. Although the optical breakthroughs 8 of the partial lattice G2 are each immediately adjacent to optical breakthroughs of the partial lattice G1, they do not have any immediate neighbors within their own partial lattice G2. With a suitable selection of the partial lattices G1 and G2, the cut 9 is then complete. In the division shown in the Figure, however, a third partial lattice G3 is provided, too.

A further coordinate transformation of the control unit of the instrument 2 ensures that, in a third pass, optical breakthroughs are generated at the points of the partial lattice G3, each of said optical breakthroughs filling any gaps still remaining between the plasma bubbles 8 of the partial lattices G1 and G2. As a result, the surface lattice-type array F is completely filled with plasma bubbles 8 so that the cut 9 is finished.

If a partial lattice is used for processing the points where plasma bubbles 8 for the cut 9 have to be initiated, this has the advantage that the control unit of the instrument 2 can work with a fixed deflection scheme, which merely has to be subjected to a fixed coordinate transformation for processing the partial lattices G1, G2 and G3. At the same time, it is ensured that no point of the surface lattice-type array F remains without a plasma bubble 8.

The invention claimed is:

1. A method of producing cuts in a transparent material, comprising:

generating optical breakthroughs in the material by application of laser radiation focused into the material at a focal point; the laser radiation passing through the surface of the material without injuring the surface of the material and the optical breakthroughs being formed within the material proximate the focal point;

shifting the focal point three dimensionally within the material so as to form the cut by a surface lattice-type array of sequentially arranged optical breakthroughs;

shifting the focal point along a three dimensional path within the material such that adjacent optical breakthroughs are not generated immediately following each other along said path; and wherein the surface lattice-type array of the optical breakthroughs is made up of at least two partial lattices including at least a first partial lattice and a second partial lattice, which are processed one after another, with respect to their associated optical breakthroughs; and wherein there is a gap between sequentially generated optical breakthroughs of each partial lattice, the gap being such that plasma bubbles generated in the material by sequential optical breakthroughs of each partial lattice do not merge and wherein plasma bubbles of the first partial lattice are adjacent plasma bubbles of the second partial lattice.

2. The method as claimed in claim 1, wherein the transparent material comprises the cornea of an eye.

3. The method as claimed in claim 1, further comprising selecting three partial lattices such that, in the surface lattice-type array for at least one optical breakthrough, in at least one partial lattice all adjacent optical breakthroughs belong to other partial lattices.

4. The method as claimed in claim 3, wherein for all partial lattices, the optical breakthroughs do not have an immediately adjacent optical breakthrough belonging to the same partial lattice.

5. The method as claimed in claim 1, further comprising generating the cut by a surface lattice-type array in the shape of a trigonal lattice, and
generating three partial lattices from one partial lattice template by three different displacements of the template along an axis of said partial lattice template.

6. A device for producing cuts in a transparent material, comprising:
a source of laser radiation, which focuses laser radiation into the material and causes optical breakthroughs therein, the laser radiation being such that it passes through a surface of the material without injuring the surface of the material and such that the optical breakthroughs form within the material;
a scanning unit, which shifts the focal point;
a control unit which controls the scanning unit to shift the focal point in three dimensions within the material so as to form the cut by a surface lattice-type array of sequentially arranged optical breakthroughs in the material, said control unit shifting the focal point along a three dimensional path within the material and not generating adjacent optical breakthroughs immediately following each other along said three dimensional path;
wherein the surface lattice-type array of the optical breakthroughs is made up of at least two partial lattices including at least a first partial lattice and a second partial lattice and the control unit effects three dimensional focus shifting such that the partial lattices are processed one after another, with respect to their associated optical breakthroughs; and
wherein there is a gap between sequentially generated optical breakthroughs of each partial lattice, the gap being such that plasma bubbles generated in the material by sequential optical breakthroughs of each partial lattice do not merge and wherein plasma bubbles of the first partial lattice are adjacent plasma bubbles of the second partial lattice.

7. The device as claimed in claim 6, wherein the transparent material comprises cornea of an eye.

8. The device as claimed in claim 6, wherein the control unit selects the partial lattices such that, in at least one partial lattice for at least one optical breakthrough, all adjacent optical breakthroughs belong to other partial lattices.

9. The device as claimed in claim 8, wherein for all partial lattices, the optical breakthroughs do not have an immediately adjacent optical breakthrough belonging to the same partial lattice.

10. The device as claimed in claim 6, wherein the control unit generates the cut by generating a surface lattice-type array in the form of a trigonal lattice and generates three partial lattices from a partial lattice template by three different displacements of the template along an axis of said partial lattice template.

11. A method of producing cuts in a cornea, comprising:
sequentially generating a series of optical breakthroughs in the cornea by application of laser radiation that passes through a surface of the cornea without injuring the surface of the cornea and that is focused into the cornea at a focal point within the cornea;
sequentially shifting the focal point in three dimensions within the cornea along a predefined surface lattice array so as to form the cut;
predefining the surface lattice array and sequence of three dimensional shifting such that adjacent optical breakthroughs are not sequentially generated immediately following each other and a time delay exists between the formation of the adjacent optical breakthroughs sufficient for a plasma bubble formed at a preceding optical breakthrough to collapse prior to generation of a following adjacent optical breakthrough; and
wherein the surface lattice-type array of the optical breakthroughs is made up of at least two partial lattices including at least a first partial lattice and a second partial lattice, which are processed one after another; and
predefining the surface lattice array such that there is a gap between sequentially generated optical breakthroughs of each partial lattice, the gap being such that plasma bubbles generated in the material by sequential optical breakthroughs of each partial lattice do not merge and wherein plasma bubbles of the first partial lattice are adjacent plasma bubbles of the second partial lattice.

12. The method as claimed in claim 11, further comprising selecting three partial lattices such that, in the surface lattice-type array for at least one optical breakthrough, in at least one partial lattice all adjacent optical breakthroughs belong to other partial lattices.

13. The method as claimed in claim 11, wherein for all partial lattices, the optical breakthroughs do not have an immediately adjacent optical breakthrough belonging to the same partial lattice.

14. The method as claimed in claim 11, further comprising generating the cut by a surface lattice-type array in the shape of a trigonal lattice, and
generating three partial lattices from one partial lattice template by three different displacements of the template along an axis of said partial lattice template.

15. A method of producing cuts in a transparent material, comprising the steps of:
generating internal cuts within the material by application of laser radiation focused into the material at a focal point;
selecting the laser radiation such that the laser radiation passes through a surface of the material and into the material without creating injury to the surface of the material and such that optical breakthroughs are formed at the focal point thus creating the internal cuts;
shifting the focal point three dimensionally within the material so as to form the cut by a surface lattice-type array of sequentially arranged optical breakthroughs;
shifting the focal point three dimensionally along a path such that adjacent optical breakthroughs are not generated immediately following each other along said path; and
wherein the surface lattice-type array of the optical breakthroughs is made up of at least two partial lattices including at least a first partial lattice and a second partial lattice, which are processed one after another, with respect to their associated optical breakthroughs; and
shifting the focal point such that there is a gap between sequentially generated optical breakthroughs of each partial lattice, the gap being such that plasma bubbles generated in the material by sequential optical breakthroughs of each partial lattice do not merge and wherein plasma bubbles of the first partial lattice are adjacent plasma bubbles of the second partial lattice.

16. The method as claimed in claim 15, wherein the transparent material comprises the cornea of an eye.

17. The method as claimed in claim 15, further comprising selecting three partial lattices such that, in the surface lattice-type array for at least one optical breakthrough, in at least one partial lattice all adjacent optical breakthroughs belong to other partial lattices.

18. The method as claimed in claim 17, wherein for all partial lattices, the optical breakthroughs do not have an immediately adjacent optical breakthrough belonging to the same partial lattice.

19. The method as claimed in claim 15, further comprising generating the cut by a surface lattice-type array in the shape of a trigonal lattice, and generating three partial lattices from one partial lattice template by three different displacements of the template along an axis of said partial lattice template.

* * * * *

UNITED STATES PATENT AND TRADEMARK OFFICE
CERTIFICATE OF CORRECTION

PATENT NO.       : 8,597,281 B2
APPLICATION NO.  : 10/566008
DATED            : December 3, 2013
INVENTOR(S)      : Bischoff et al.

It is certified that error appears in the above-identified patent and that said Letters Patent is hereby corrected as shown below:

On the Title Page under Item (75) Inventors: it should read as follows:

Mark Bischoff, Jena (DE); Dirk Mühlhoff, Jena (DE); Mario Gerlach, Glienicke-Nordbahn (DE); Carsten Lang, Eisenberg (DE); Markus Sticker, Jena (DE); Michael Bergt, Weimar (DE)

In the Specification

Col. 2, line 30, delete "us" and insert --µs--

Signed and Sealed this
Twelfth Day of August, 2014

Michelle K. Lee
*Deputy Director of the United States Patent and Trademark Office*